United States Patent
Boussignac

(10) Patent No.: US 6,575,166 B2
(45) Date of Patent: Jun. 10, 2003

(54) TRACHEAL CATHETER

(76) Inventor: Georges Boussignac, 1, Avenue de Provence, 92160 Antony (FR)

(*) Notice: Subject to any disclaimer, the term of this patent is extended or adjusted under 35 U.S.C. 154(b) by 0 days.

(21) Appl. No.: 09/242,281
(22) PCT Filed: Jun. 29, 1998
(86) PCT No.: PCT/FR98/01379
§ 371 (c)(1),
(2), (4) Date: Feb. 12, 1999
(87) PCT Pub. No.: WO99/01170
PCT Pub. Date: Jan. 14, 1999

(65) Prior Publication Data
US 2002/0179090 A1 Dec. 5, 2002

(30) Foreign Application Priority Data
Jun. 30, 1997 (FR) .............................. 97 08187

(51) Int. Cl.[7] ................................................ A62B 9/06
(52) U.S. Cl. ............................ 128/207.14; 128/204.18; 128/200.24
(58) Field of Search ...................... 128/200.24, 203.12, 128/204.18, 205.19, 207.14, 207.18

(56) References Cited

U.S. PATENT DOCUMENTS

| 3,991,762 | A | * | 11/1976 | Radford | 128/207.14 |
|---|---|---|---|---|---|
| 4,300,550 | A | * | 11/1981 | Gandi et al. | 128/207.18 |
| 5,029,580 | A | | 7/1991 | Radford et al. | |
| 5,088,486 | A | * | 2/1992 | Jinotti | 128/207.14 |
| 5,125,893 | A | * | 6/1992 | Dryden | 128/207.14 |
| 5,140,983 | A | | 8/1992 | Jinotti | |
| 5,167,622 | A | | 12/1992 | Muto | |
| 5,555,880 | A | * | 9/1996 | Winter et al. | 128/204.21 |
| 5,582,163 | A | * | 12/1996 | Bonassa | 128/204.26 |

* cited by examiner

Primary Examiner—Glenn K. Dawson
(74) Attorney, Agent, or Firm—Fisher, Christen & Sabol

(57) ABSTRACT

A ventilation tube incorporating an aspiration probe for aspirating pulmonary phlegm for a patient under artificial ventilation. The probe has a channel permanently blowing a pressurized breathing mixture through a distal orifice laterally disposed and sufficiently distant from the distal end of the probe to be located opposite the ventilation tube inner wall so as to diffuse the blown air. The probe is connected to an aspiration device to aspirate the phlegm from the pulmonary system.

17 Claims, 1 Drawing Sheet

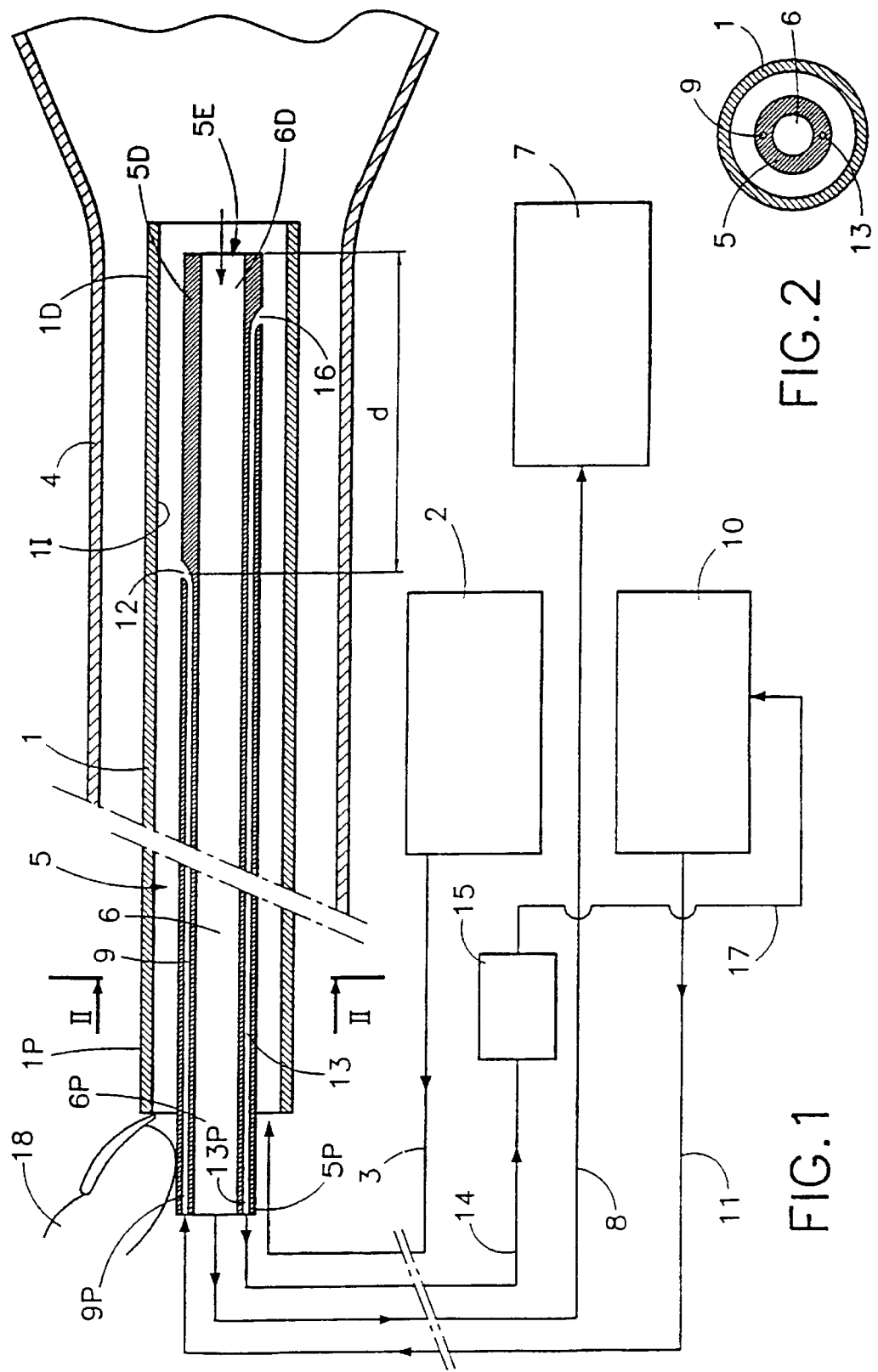

TRACHEAL CATHETER

The present invention relates to an endotracheal aspiration probe for a patient under artificial ventilation.

It is known that a patient under artificial ventilation is connected to an artificial respiration apparatus by way of a ventilation tube placed in his trachea and supplied with respiratory gas by said apparatus. Such a patient secretes pulmonary mucus which requires to be eliminated several times a day. Probes are also already known for aspirating this pulmonary mucus. Depending on the design of the ventilation tube, such a probe can be introduced into the trachea either as a replacement for said ventilation tube, or through the latter, and the artificial ventilation must either be interrupted or, by contrast, can be maintained during aspiration of the mucus.

However, even in the most favorable case in which the artificial ventilation is maintained during the aspiration of the mucus, there are not inconsiderable risks of the patient suffering hypoxia, which can cause the heart to slow down, or even arrest, and these risks are due to the fact that an artificial respirator insufflates respiratory gas only about one third of the time. Thus, during the other two thirds of the time, the aspiration of the pulmonary mucus can lead to pulmonary collapse.

SUMMARY OF THE INVENTION

The object of the present invention is to completely eliminate the risks of hypoxia during aspiration of pulmonary mucus from a patient under artificial ventilation.

To this end, according to the invention, the endotracheal aspiration probe for aspirating pulmonary mucus from a patient under artificial ventilation, connected to an artificial respiration apparatus by way of a ventilation tube placed in his trachea, said aspiration probe being intended to be connected to aspiration means and to be introduced into said ventilation tube, is distinguished by the fact that it includes a channel for permanent blowing of a respiratory gas under pressure, and that the distal orifice of said blowing channel is lateral and sufficiently distant from the distal end of said probe to be situated opposite the inner wall of said ventilation tube, even when said probe occupies its position of maximum insertion inside said ventilation tube.

Thus, during aspiration of the pulmonary mucus, respiratory gas is insufflated into the patient's trachea so that a pulmonary collapse cannot take place. Moreover, because the distal orifice of the blowing channel is situated opposite the inner wall of the ventilation tube, this blown gas cannot damage the tracheal and bronchial mucous membranes.

To achieve this result, it is advantageous, in the case of an adult, for the distance between the distal orifice of the blowing channel and the distal end of the aspiration probe to be equal to at least 10 cm, and preferably at least approximately equal to 15 cm. If the probe is intended for a young child, this distance can be at least equal to 2 cm.

It is advantageous to provide, in said aspiration probe, a channel which is used for measuring pulmonary pressure and opens out in the vicinity of the distal end of the aspiration probe, and to use the pressure in said channel for measuring pressure in order to adjust the flow rate of the respiratory gas so as to prevent pulmonary collapse.

The gas being blown can be oxygen, for example.

In an advantageous embodiment, the blowing channel and/or the channel for measuring pressure are formed in the wall of said aspiration probe.

Advantageously, the pressure of the respiratory gas being blown is chosen at most equal to 3.5 bar, while the under pressure at the distal end of the aspiration probe is of the order of several hundreds of millibars.

The figures in the attached drawing will show clearly how the invention can be realized. In these figures, identical references designate similar elements.

BRIEF DESCRIPTION OF THE INVENTION

FIG. 1 is a diagrammatic longitudinal section through the endotracheal aspiration probe according to the present invention, in place in a ventilation tube.

FIG. 2 is a section along the line II—II in FIG. 1.

DETAILED DESCRIPTION OF THE INVENTION

In FIG. 1, a ventilation tube 1 is shown in diagrammatic representation, connected to an artificial respirator 2 by way of a connection line 3 and intended to ventilate a patient, only the trachea 4 of the patient being shown. For this purpose, the distal part 1D of said ventilation tube 1 is lodged in said trachea 4, while the proximal part 1P of the ventilation tube 1 protrudes from the patient's mouth (not shown), is situated outside the latter and is connected to said artificial respirator 2 via the connection line 3.

A probe 5 for aspirating pulmonary mucus from the patient can be introduced into the ventilation tube 1. The probe 5 includes a central longitudinal lumen 6, the proximal part 6P of which is connected to an aspirator 7 via a connection line 8. The aspirator 7 creates an underpressure, for example equal to several hundreds of millibars, at the distal end 5E of said probe 5.

The aspiration probe 5 is provided with a first longitudinal channel 9, for example formed in the thickness of its wall, and the proximal part 9P of which is connected via a connection line 11 to a source 10 of respiratory gas under pressure. The longitudinal channel 9 opens out in the wall of the probe 5 via a lateral orifice 12 formed in the distal part 5D of said probe, but at a distance d from the distal end 5E thereof. If the probe 5 is intended for an adult, the distance d can be of the order of 10 cm to 15 cm. The source 10 delivers to the first longitudinal channel 9 a blown gas, for example oxygen-based, so that a jet of respiratory gas, permanent during aspiration, emerges from the lateral orifice 12. The pressure of this jet of respiratory gas is at most equal to 3.5 bar.

The aspiration probe 5 is moreover provided with a second longitudinal channel 13, for example formed in the thickness of its wall, and the proximal part 13P of which is connected to a pressure sensor 15 via a connection line 14. The longitudinal channel 13 opens out in the wall of the probe 5 via a lateral orifice 6, formed in the distal part 5D of the probe 5, in the vicinity of said distal end 5E.

The pressure sensor 15 is connected to the source 10 via a connection line 17.

The aspiration probe 5 is, for example, held by hand by an operator (not shown) whose fingers 18 grip the proximal end 5P of said probe.

In FIG. 1, the aspiration probe 5 is represented already in place in the artificial ventilation tube 1. It is held at its proximal end 5P by the fingers 18 of said operator, said fingers bearing against the proximal end 1P of the endotracheal tube 1, which defines the maximum insertion of said probe 5 into said tube 1.

Even in this position of maximum insertion, the blowing orifice 12 is situated opposite the inner wall 1I of the tube 1, so that the permanent jet of the blown gas emerging from said orifice 12 strikes this inner wall and is diffused by the tube 1 toward the patient's lungs, without any possibility of damage to the tracheal and bronchial mucous membranes.

The pressure of the respiratory gas in the patient's lungs is captured via the orifice 16 and transmitted through the channel 13 and the connection line 14 to the pressure sensor 15 which, via the connection line 17, can control the delivery rate of the source 10 so as to adjust it to a value which is such that all hypoxia is prevented.

Thus, it is always possible to optimize the pressure of respiratory gas in the patient's lungs during the aspiration of the mucus through the lumen 6 of the probe 5, by way of the aspirator 7 and the connection line 8.

It will be readily appreciated that the aspiration probe 5 can be easily introduced into the tube 1 (FIG. 1) or removed therefrom.

What is claimed is:

1. An endotracheal assembly for a patient necessitating an artificial ventilation, said assembly comprising:

a ventilation tube having a proximal end intended to be connected to an artificial respiration apparatus and a distal end intended to be placed in the trachea of said patient;

an aspiration probe for aspirating pulmonary mucus from said patient, said aspiration probe having a proximal end intended to be connected to aspiration means and a distal end intended to be inserted into said ventilation tube, said aspiration means being able to generate an underpressure at the distal end of said aspiration probe, and said aspiration probe comprising a blowing channel for permanent blowing of a respiratory gas under pressure, said blowing channel having a proximal end intended to be connected to a source of such a respiratory gas and a distal orifice disposed laterally in relation with said aspiration probe, at a distance from the distal end thereof, so that, in use, said distal orifice of said blowing channel is situated opposite of the inner wall of said ventilation tube so that the jet of the blow respiratory gas emerging from said distal orifice strikes the inner wail of the ventilation tube and is diffused by the ventilation tube, without any possibility of damage to the tracheal and bronchial mucous membranes of said patient.

2. The assembly according to claim 1, intended for an adult, wherein the distance (d) between the distal orifice of the blowing channel and the distal end of said aspiration probe is equal to at least 10 cm.

3. The assembly according to claim 2, wherein said distance (d) is at least approximately equal to 15 cm.

4. The assembly according to claim 1, wherein the assembly includes a channel which is used for measuring pulmonary pressure and opens out in the vicinity of the distal end of said aspiration probe.

5. The assembly according to claim 4, wherein the pressure in said channel for measuring pulmonary pressure controls the flow rate of the respiratory gas being blown.

6. The assembly according to claim 4, wherein said channel for measuring pressure is formed in the wall of said/robe.

7. The assembly according to claim 1, wherein said respiratory gas being blown is oxygen-based.

8. The assembly according to claim 1, wherein said blowing channel is formed in the wall of said probe.

9. The assembly according to claim 1, wherein the pressure of the respiratory gas being blown is less than 3.5 bar.

10. The assembly according to claim 1, wherein the underpressure at the distal end of said aspiration probe is of the order of several hundreds of millibars.

11. An endotracheal assembly for a patient necessitating an artificial ventilation, said assembly comprising:

a ventilation tube having a proximal end intended to be connected to an artificial ventilation respiration apparatus and a distal end intended to be placed in the trachea of said patient;

an aspiration probe for aspirating pulmonary mucus from said patient; said aspiration probe having a proximal end intended to be connected to aspiration means and a distal end intended to be inserted into said ventilation tube, said aspiration means being able to generate an underpressure at the distal end of said aspiration probe, and said aspiration probe comprising:

a blowing channel for permanent blowing of a respiratory gas under pressure, said blowing channel having a proximal end intended to be connected to a source of such a respiratory gas and a distal orifice disposed laterally in relation with said aspiration probe, at a distance from the distal end thereof, so that, in use, said distal orifice of said blowing channel is situated opposite of the inner wall of said ventilation tube so that a jet of the respiratory gas emerging from said distal orifice strikes the inner wall of the ventilation tube and is diffused by the ventilation tube, without any possibility of damage of the tracheal and bronchial mucous membranes of said patient; and a second longitudinal channel which is formed in the wall of said aspiration probe, which opens out in the vicinity of the distal end of said aspiration probe and which is used for measuring pulmonary pressure; and a pressure sensor which is connected to the proximal part of the second longitudinal channel, which measures pulmonary pressure and which controls the flow rate of the respiratory gas so as to adjust it to a value which is such that all hypoxia is prevented.

12. The assembly according to claim 11, intended for an adult, wherein the distance (d) between the distal orifice of the blowing channel and the distal end of said aspiration probe is equal to at least 10 cm.

13. The assembly according to claim 12, wherein said distance (d) is at least approximately equal to 15 cm.

14. The assembly according to claim 11, wherein said respiratory gas being blown is oxygen-based.

15. The assembly according to claim 11, wherein said blowing channel is formed in the wall of said probe.

16. The assembly according to claim 11, wherein the pressure of the respiratory gas being blown is less than 3.5 bar.

17. The assembly according to claim 11, wherein the underpressure at the distal end of said aspiration probe is of the order of several hundreds of millibars.

* * * * *